United States Patent
Lange et al.

(10) Patent No.: US 10,864,317 B2
(45) Date of Patent: Dec. 15, 2020

(54) TIME CONTROLLED PERIODIC INFUSION

(71) Applicant: Ferrosan Medical Devices A/S, Søborg (DK)

(72) Inventors: Kai Lange, Birkerød (DK); Christian Rothe, Hundested (DK); Frederik Sonnenborg, Jyllinge (DK); Arnt Larsen Lund, Sorø (DK); Søren Falkesgaard Ørts, Virum (DK); Claus Reuber, Roskilde (DK)

(73) Assignee: Ferrosan Medical Devices A/S, Søborg (DK)

( * ) Notice: Subject to any disclaimer, the term of this patent is extended or adjusted under 35 U.S.C. 154(b) by 444 days.

(21) Appl. No.: 15/517,674

(22) PCT Filed: Oct. 28, 2015

(86) PCT No.: PCT/EP2015/074982
§ 371 (c)(1),
(2) Date: Apr. 7, 2017

(87) PCT Pub. No.: WO2016/066686
PCT Pub. Date: May 6, 2016

(65) Prior Publication Data
US 2018/0296753 A1    Oct. 18, 2018

(30) Foreign Application Priority Data
Oct. 28, 2014   (EP) .................................. 14190669

(51) Int. Cl.
*A61M 1/00* (2006.01)
*A61M 31/00* (2006.01)
(Continued)

(52) U.S. Cl.
CPC ......... *A61M 5/1424* (2013.01); *A61K 9/0019* (2013.01); *A61K 31/167* (2013.01);
(Continued)

(58) Field of Classification Search
CPC .......... A61M 2005/14208; A61M 2205/3334; A61M 2205/52; A61M 2205/8206;
(Continued)

(56) References Cited

U.S. PATENT DOCUMENTS 5,681,285 A    10/1997  Ford et al.
5,795,327 A *   8/1998  Wilson .................. A61M 5/172
                                                              604/65
(Continued)

FOREIGN PATENT DOCUMENTS

EP    1 583 571 B1    2/2008
EP    2 047 876 A1    4/2009
(Continued)

OTHER PUBLICATIONS

International Search Report and Written Opinion for International Application No. PCT/EP2015/074982; Hillerod Hospital; dated Feb. 8, 2016; 12 pages.
(Continued)

*Primary Examiner* — Rebecca E Eisenberg
(74) *Attorney, Agent, or Firm* — Hamilton, Brook, Smith & Reynolds, P.C.

(57) ABSTRACT

The present disclosure relates to administration of fluid medication, in particular medication and dosing regimen for management of pain, more specifically to an anesthetic and dosing regimen for anesthetic for perioperative pain management and/or for palliative care. The present disclosure relates further to a medication pump and a method for delivering medication using the medication pump.

19 Claims, 10 Drawing Sheets

(51) Int. Cl.
*A61M 5/142* (2006.01)
*A61M 5/168* (2006.01)
*A61K 9/00* (2006.01)
*A61K 31/167* (2006.01)
*A61K 31/445* (2006.01)
*A61M 5/145* (2006.01)

(52) U.S. Cl.
CPC ......... *A61K 31/445* (2013.01); *A61M 5/1452* (2013.01); *A61M 5/14248* (2013.01); *A61M 5/16854* (2013.01); *A61M 5/14244* (2013.01); *A61M 2005/14208* (2013.01); *A61M 2202/048* (2013.01); *A61M 2205/3334* (2013.01); *A61M 2205/3584* (2013.01); *A61M 2205/52* (2013.01); *A61M 2205/8206* (2013.01)

(58) Field of Classification Search
CPC ............ A61M 5/1424; A61M 5/14244; A61M 5/14248; A61M 5/142; A61M 5/1723; G06F 19/3468
See application file for complete search history.

(56) References Cited

U.S. PATENT DOCUMENTS

| | | | |
|---|---|---|---|
| 6,231,560 B1* | 5/2001 | Bui | A61M 5/1723 604/500 |
| 6,579,280 B1 | 6/2003 | Kovach et al. | |
| 9,138,534 B2 | 9/2015 | Yodfat et al. | |
| 2003/0163223 A1 | 8/2003 | Blomquist | |
| 2006/0135940 A1* | 6/2006 | Joshi | A61M 5/168 604/500 |
| 2007/0088269 A1 | 4/2007 | Valego et al. | |
| 2010/0094251 A1 | 4/2010 | Estes | |
| 2010/0152713 A1 | 6/2010 | Adler et al. | |
| 2010/0298685 A1* | 11/2010 | Hayter | A61B 5/14532 600/365 |
| 2011/0275410 A1 | 11/2011 | Caffey et al. | |
| 2012/0029333 A1* | 2/2012 | Dogwiler | A61M 5/158 600/365 |
| 2013/0006171 A1* | 1/2013 | Griessmann | A61M 1/166 604/29 |
| 2013/0204202 A1 | 8/2013 | Trombly et al. | |
| 2014/0025039 A1 | 1/2014 | Rajendran et al. | |
| 2015/0363097 A1 | 12/2015 | Draper et al. | |

FOREIGN PATENT DOCUMENTS

| | | |
|---|---|---|
| WO | WO 2004/056412 | 7/2004 |
| WO | WO 2004/093648 | 11/2004 |
| WO | WO 2005/118032 | 12/2005 |
| WO | WO 2006/023636 A1 | 3/2006 |
| WO | WO 2006/086723 | 8/2006 |
| WO | WO 2007/119178 | 10/2007 |
| WO | WO 2008/019016 A2 | 2/2008 |
| WO | WO 2008/139458 A2 | 11/2008 |
| WO | WO 2012/040528 A1 | 3/2012 |

OTHER PUBLICATIONS

International Preliminary Report on Patentability for International Application No. PCT/EP2015/074982, "Time-Controlled Periodic Infusion" Date of completion of report: Sep. 23, 2016.

* cited by examiner

TIME CONTROLLED PERIODIC INFUSION

RELATED APPLICATIONS

This application is the U.S. National Stage of International Application No. PCT/EP2015/074982, filed Oct. 28, 2015, which designates the U.S., published in English, and claims priority under 35 U.S.C. §§ 119 or 365(c) to EP Application No. 14190669.3, filed Oct. 28, 2014. The entire teachings of the above applications are incorporated herein by reference.

FIELD OF INVENTION

The present disclosure relates to administration of fluid medication, in particular medication and dosing regimen for management of pain, more specifically to an anesthetic and dosing regimen for anesthetic for perioperative pain management and/or for palliative care. The present disclosure relates further to a medication pump and a method for delivering medication using the medication pump.

BACKGROUND OF INVENTION

During and after surgery of a patient it may be required to provide the patient with a continuous flow of medication through a catheter over a period of time where pain may occur. Typically, the provision of medication is done at hospitals by using either a rapid injection of a bolus of medication from a syringe or by a slow infusion of the medication with a continuous flow using a stationary pumping device.

Several problems are related to these two methods of dosing regimens. During a rapid injection, there might be delivered too much of the medication, such that the medication diffuses to locations out of the area of interest, resulting in the medication might not work, or even cause several side effects to the patient. During a slow infusion, typically constantly infused over time, there is a risk of not reaching a sufficient concentration gradient to facilitate optimal transportation of the active substances into the targeted area such as the nerve. Hence, the drug will be poorly utilized in regards to effect vs. consumption.

Furthermore, in relation to dosing regimen, a catheter is typically placed close to the nerves of interest in order to block these. For proper blocking it is then typically required that a rather large bolus of medication is infused into the patient via the catheter and further into the vicinity of the nerves.

As an example of medication is local anesthetic (LA), which may be injected around nerves to block the nerve conduction for a period of time. LA will leave a patient pain free after trauma or surgery. The most used ways of administering LA are:
 1) a bolus injection over 10-15 seconds;
 2) a continuous infusion; or
 3) a combination of the two.

Today bolus injections range from 10 to 40 mL (infusion rate: 2,400-14,400 mL/h). Continuous infusion rates are typically in the range of 5-10 mL/h.

The administration of large volumes of LA to patients is problematic for several reasons. Large volumes of LA are toxic and may result in cardiac arrest. A bolus injection of 40 mL may be close to a toxic dose. A continuous infusion of 10 mL/h results in 240 mL of LA administered over 24 h.

Several problems are related to a large medication bolus. First of all, a large bolus may not be required if the peripheral catheter is placed correctly, secondly, the effect may not be improved despite of a larger volume, and thirdly, the large medication bolus may cause side effects. Finally, the medication may be highly expensive, and there is thus a need for an optimal dosing regimen.

In relation to the pumping device, there is a problem in terms of the operation of the pumping device. Generally, two types of devices are on the market; simple, single use devices and more expensive, multiple use, complex devices. The prior art single use devices typically have a limited precision in terms of dosing volume and flow consistency over time and limited means of adjusting dosing settings. The more complex prior art devices are more precise but require educated personal to control and set up the device, and because of this, the patient is forced to be hospitalized or a complex logistic set up must be arranged to handle the returning, cleaning and maintenance of the pumps. The simple, cheaper devices for single use are more commonly used to be taken home with the patient when discharged from the hospital. The drawback of these devices is typically the limited precision as mentioned above.

Moreover, the large volumes used in the current dosing regimens make today's infusion devices bulky. There is therefore a clear interest in developing a compact system to provide safe and satisfactory pain relief.

Thus, there is a great need for an improved device and corresponding dosing regimen that also addresses the home care segment without compromising the system performance.

SUMMARY OF INVENTION

The present disclosure relates to a new dosing regimen for administration of local anesthetic (LA) drug through catheters.

Research has shown that it is possible to provide pain relief with substantially lower bolus volumes of LA without compromising block duration. A bolus injection of 1-2 ml LA is sufficient for peripheral nerve blocks in the upper limb and 8 mL of LA is sufficient to block the largest peripheral human nerve, the sciatic nerve.

The duration of pain relief for nerve blocks using ropivacaine as LA is about 12 h. However, block duration is dependent on regional and individual differences.

It is assumed that diffusion of LA plays a major role in blocking a nerve although some kind of active transport may also take place. Either way, it is important for the LA to be in close contact with the nerve. If LA is administered as a large bolus, most of the LA will never come into close contact with the nerve, because it will spread into adjacent tissue. A large volume administered as a bolus will spread into adjacent tissue and will never block the nerve. On the other hand, a continuous infusion may be too slow to maintain a sufficient concentration gradient to block the nerve.

In order to overcome the issues as just described, one aspect of the present invention is to provide a new dosing regimen for administration of local anesthetics, in particular a local and/or regional anesthetic for use in perioperative pain management administered as a 1-20 mL time-controlled periodic infusion by a catheter, wherein each time-controlled periodic infusion is a preset infusion sequence that is administered during 1-20 minutes, administered with flow rates between 30 mL/h and at least 150 mL/h, preferably between 30 mL/h and 1200 mL/h and separated by 1-24, preferably separated by 1-48 hours. However, the new dosing regimen may also be for use in palliative care.

According to the present invention as defined by the new dosing regimen, there is provided a better way to administer LA. The new dosing regimen is between a bolus injection and a continuous infusion.

Another embodiment relates to a local and/or regional anesthetic for perioperative pain management administered as a 1-20 mL time-controlled periodic infusion by a catheter, wherein the time-controlled periodic infusion is administered during 1-20 minutes with a (continuous) flow rate from 1.5 mL/h-150 mL/h and where each time-controlled periodic infusion is separated by 1-24 hours.

An effect of having the dosing regimen as disclosed herein is that at a greater part of the medication is able to have the medical effect on exactly the location as it is supposed to.

A second aspect of the present invention is to provide a catheter for delivering the anesthetic drug as just described.

A third aspect of the present invention is to provide a wearable administration system for delivering a time-controlled periodic infusion of medication to a target, comprising: a medication pump; a control unit configured to automatically operate said medication pump to periodically infuse said medication in an infusion volume between 1-20 mL during an infusion time between 1-20 minutes with a preset infusion sequence utilizing flow rates between 30 mL/h and at least 150 mL/h, preferably between 30 mL/h and 1200 mL/h and with a period of 1-24 hours, preferably with a period of 1-48 hours.

Another embodiment relates to wearable administration system configured for delivering a time-controlled periodic infusion of medication to a target, comprising: a medication pump; a control unit configured to automatically operate said medication pump to periodically infuse said medication in an infusion volume between 1-20 mL during an infusion time between 1-20 minutes with a (continuous) flow rate between 1.5 mL/h-150 mL/h and with a period of 1-24 hours.

According to the third aspect of the invention, the meaning of wearable is to be understood as a system that can be carried on a body, for example attached on a body or on clothes. The wearable administration system is not intended for being inserted into a body. In other words, by wearable is not meant a system that can be carried inside the body.

An effect of using the specified dosing regimen, as here disclosed, is that the total volume of drug delivered is relatively small in comparison to conventional dosages, and said volume can be contained in a small pump, meaning that the pump may be easy to wear. Further, by having a wearable device, comprising the pump, the treatment can take place outside the hospital, for example at home.

In a fourth aspect of the present invention, there is a delivery system for delivering a time-controlled periodic infusion of medication to a target, comprising: a wearable administration system as described in the third aspect; and a catheter.

A fifth aspect is related to a method for delivering a time-controlled periodic infusion of medication to a target from a wearable administration system comprising a medication pump and a control unit, comprising the steps of: infusing said medication by an infusion volume between 1-20 mL during an infusion time between 1-20 minutes with a preset infusion sequence utilizing flow rates between 30 mL/h-1200 mL/h by automatically operating said pump via said control unit; waiting a period of 1-48 hours; and repeating the steps.

DETAILED DESCRIPTION OF THE INVENTION

Figure 1:
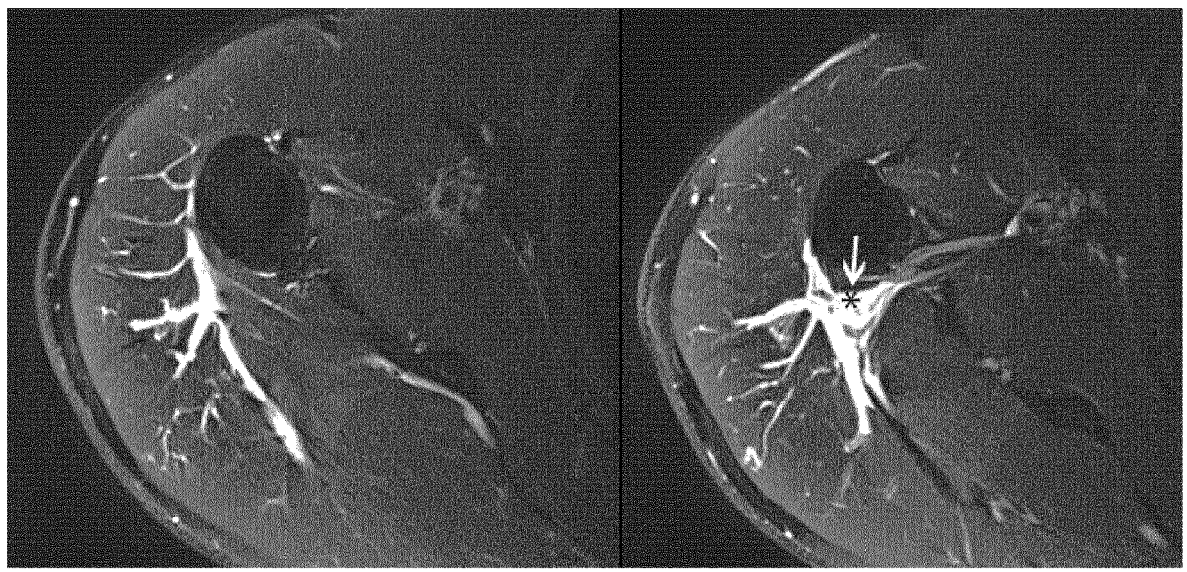
FIG. 1 shows how medication is diffused around the axillary nerve in the shoulder region using a dosing regimen according to prior art.

As previously described, the present disclosure relates to a new dosing regimen for administration of local anesthetics through catheters.

Dosing Regimen

By the present invention according to the dosing regimen, pilot studies have shown that as little as 1-2 mL of LA (infusion rate: 480 mL/h) spreads up to 10 cm along the median nerve in the upper limb and 1 mL of LA (infusion rate: 720 mL/h) blocks of the common peroneal nerve in the lower limb and spreads at least 5 cm along the nerve. Thus, by the present invention, there is provided an efficient dosing regimen that is sufficient for nerve blocking.

In one embodiment of the invention, the flow rate may not be constant and may be variable and/or dependent on the given management of pain. Several embodiments of infusion sequences are described in the following.

In a first embodiment, the preset infusion sequence is defined by a constant flow rate.

In a second embodiment, the preset infusion sequence is defined by an increasing flow rate.

In a further embodiment, the preset infusion sequence is defined by a decreasing flow rate.

In an alternative and/or additional embodiment, the preset infusion sequence is defined by a plurality of pulses with constant flow rate.

In another alternative and/or additional embodiment, the preset infusion sequence is defined by a plurality of pulses with increasing flow rate.

In yet another alternative and/or additional embodiment, the preset infusion sequence is defined by a plurality of pulses with decreasing flow rate.

In preferred embodiments, the preset infusion sequence is defined by a combination of the preset infusion sequences as described above.

In a preferred embodiment of the dosing regimen, the anesthetic is chosen from the group of ropivacaine, bupivacaine, mepivacaine, lidocaine and/or any other local anesthetic drug. Ropivacaine and bupivacaine may be effective for about 12 hours or longer for peripheral nerve blocking and 1-2 hours for epidural nerve blocking.

The catheter to be used may be a peripheral indwelling catheter or an epidural catheter. Preferably, the indwelling catheter is an indwelling catheter as described by the article 'A novel concept for continuous peripheral nerve blocks. Presentation of a new ultrasound guided device', in Acta Anaesthesiologica Scandinavica by C. Rothe et al. (2014). A suitable indwelling catheter is also described in U.S. application No. 61/912,262 filed 5 Dec. 2013 and entitled "Echogenic indwelling catheter". This application is hereby incorporated herein in its entirety.

When a peripheral indwelling catheter is used, for example for peripheral nerve blocking, the separation of the time-controlled periodic infusion, may for example be more than 2 hours, such as more than 3 hours, such as more than 4 hours, such as more than 5 hours, such as more than 6 hours, such as more than 7 hours, such as more than 8 hours, such as more than 9 hours, such as more than 10 hours, such as more than 11 hours, such as more than 12 hours, and/or such as up to 24 hours or more, such as up to 48 hours or more. When an epidural catheter is used, for example for epidural nerve blocking, the separation of the time-controlled periodic infusion, may for example be less than 5 hours, such as less than 4 hours, such as less than 3 hours, such as less than 2 hours, and/or such as less than 1 hours.

Preferably, the separation of the time-controlled periodic infusion may be selected according to the effective time for the given medication and the given nerve blocking as just described. The separation of the time-controlled periodic infusion, as just described, may in particular provide the desired effect. However, the infusion volume, infusion time, and flow rate all contribute to the effect, the effect being that a greater part of the medication is able to have the medical effect on exactly the location as it is supposed to.

In a preferred embodiment of the dosing regimen, the time controlled periodic infusion is an infusion volume of more than 1 mL, such as more than 2 mL, such as more than 3 mL, such as more than 4 mL, such as more than 5 mL, such as more than 6 mL, such as more than 7 mL, such as more than 8 mL, such as more than 9 mL, such as more than 10 mL, such as more than 11 mL, such as more than 12 mL, such as more than 13 mL, such as more than 14 mL or such as more than 15 mL, such as more than 16 mL, such as more than 17 mL or such as more than 18 mL, such as more than 19 mL or such as more than 20 mL.

In another preferred embodiment of the dosing regimen, the time controlled periodic infusion is an infusion volume of less than 20 mL, such as less than 19 mL, such as less than 18 mL, such as less than 17 mL, such as less than 16 mL, such as less than 15 mL such as less than 14 mL, such as less than 13 mL, such as less than 12 mL, such as less than 11 mL, such as less than 10 mL, such as less than 9 mL, such as less than 8 mL, such as less than 7 mL, such as less than 6 mL, such as less than 5 mL, such as less than 4 mL, such as less than 3 mL, such as less than 2 mL or such as less than 1 mL.

In a preferred embodiment of the dosing regimen, the duration of the infusion sequence is more than 1 min, such as more than 2 min, such as more than 3 min, such as more than 4 min, such as more than 5 min, such as more than 6 min, such as more than 7 min, such as more than 8 min, such as more than 9 min, such as more than 10 min, such as more than 11 min, such as more than 12 min, such as more than 13 min, such as more than 14 min or such as more than 15 min, such as more than 16 min, such as more than 17 min or such as more than 18 min, such as more than 19 min or such as more than 20 min.

In another preferred embodiment of the dosing regimen, the duration of the infusion sequence is less than 20 min, such as less than 19 min, such as less than 18 min, such as less than 17 min, such as less than 16 min, such as less than 15 min such as less than 14 min, such as less than 13 min, such as less than 12 min, such as less than 11 min, such as less than 10 min, such as less than 9 min, such as less than 8 min, such as less than 7 min, such as less than 6 min, such as less than 5 min, such as less than 4 min, such as less than 3 min, such as less than 2 min or such as less than 1 min.

Catheter

Related to the second aspect of the present invention, the catheter is preferably a peripheral indwelling catheter or an epidural catheter. The catheter may be a catheter as described in the first aspect of the present invention.

Administration System

Related to the third aspect of the present invention, the control unit may comprise manual operation means, configured such that when manually operated, said control unit is configured to operate said medication pump to infuse said medication in an infusion volume between 1-20 mL during an infusion time between 1-20 minutes with a preset infusion sequence utilizing flow rates between 30 mL/h-1200 mL/h. The manual operation means may for example be one or more buttons. In one embodiment of the present invention, operation of the medication pump may be activated when the manual operation means for example are pressed for more than 1 second, more than 2 seconds, more than 3 seconds, more than 4 seconds or more 5 seconds. Alternatively, manual operation means may be on an external device, for example communicating with the control unit by blue tooth, IR, NFC, USB, and/or other wireless communication technology. In this way, it may be possible for a person, such as a doctor, to read the dosing regimen from the control unit and/or the manual operation means. The manual operation means may also be a start button configured to start the time-controlled periodic infusion of medication in an automatic manner. The manual operation means may also be a stop button configured to stop the time-controlled periodic infusion of medication in an automatic manner, thereby enabling the mode where it will operate the pump when pressed for more than 1 second, more than 2 seconds, more than 3 seconds, more than 4 seconds or more 5 seconds.

The manual operation means may also be one or more buttons configured to change functionality as the user progress through a menu, state of operation or device life cycle.

According to the present invention, the preset infusion sequence as used in the administration system may be according to the infusion sequence as previously described.

In one embodiment of the administration system, the control unit is further configured to automatically operate said medication pump to periodically infuse a plurality of infusion sequences such that each of said infusion sequences are separated by a preset dwell-time that is different from the period.

In another embodiment of the administration system, the control unit is configured to alter the preset dwell-time if being operated with the manual operation means as described above.

In a preferred embodiment of the present invention, the control unit comprises manual setup means, configured such that said infusion volume, and/or infusion time and/or period is/are set up manually. The manual setup means may be one or more buttons. In order to see the infusion volume, and/or infusion time and/or period, there may be a visual display on the control unit. Alternatively, manual setup means may be on an external device, for example communicating with the control unit by blue tooth, IR, NFC, USB, and/or other wireless communication technology. The manual setup means may be the same as the manual operation means, such as for example the external device.

In another preferred embodiment of the present invention, the manual setup means is configured to be set up such that said infusion volume, and/or infusion time and/or period is/are locked. For example, after the infusion volume, and/or infusion time and/or period is/are set up, these parameters cannot be changed.

Preferably, the control unit is driven by one or more batteries, such as two AA batteries, such as two AAA batteries, such as one or more button cells and/or a portable power source. The batteries may be removable from the administration system and disposed separately. The administration system may be configured such that it remembers the setup, such that when the batteries are removed, a reset of the setup is prevented. In this way, the setup may only be required to be adjusted once and cannot be changed by a reset.

In one embodiment of the present invention, the control unit is configured to drive a rotating member, such as via a microcontroller. The rotating member may apply a pressure to the medication in the pump. The rotating member may be in liquid contact with the medication, or alternatively, the rotating member may be separated from the medication, for example by pressing on a surface which further applies pressure to the liquid. The surface may be a tube. In one embodiment, the control unit comprises an encoder system. The rotating member and/or additional controllers, such as a microcontroller, may be monitored by an encoder system. An encoder system may enable improved dosage precision compared to just operating the motor on/off using a timer, in particular since the encoder counts the number of actual motor revolutions. The encoder system may provide feedback to the control unit, for example the microcontroller, and for example in order to precisely control the dosing regimen. The rotating member may be configured to rotate in one direction only, for example to reduce suck-back, provided for example by electronic and/or mechanical control. In order to obtain great accuracy of the rotating member, the control unit may comprise a crystal controlled real timer circuit (RTC). The control unit and/or encoder may be adapted to provide information, for example via an acoustic signal and/or via a visual signal, such as on a diode or diode array, of remaining medication in the pump, for example medication in a syringe or medication in an external reservoir connected to a pump. In this sense, the pump may comprise and/or be connected a reservoir.

In a preferred embodiment of the present invention, the pump comprises a syringe, preferably comprising a piston and a piston rod. Preferably, the syringe comprises a flexible piston rod. The flexible piston rod may be bent or curled in order to decrease the total length of the device while the piston is retracted in the syringe barrel.

In another preferred embodiment of the present invention, the syringe comprises a detachable piston rod, for example attached to the piston. By having a detachable piston rod, the pump, for example comprising a syringe, may be filled directly with the medication by manually pulling the detachable piston rod. In this way, the pump can be filled like a normal syringe. Hereafter, the piston rod may be detached and the syringe may be connected to the pump and the control unit.

In yet another preferred embodiment, the insertion of the syringe into the pump housing will automatically power up and initialize the pump.

In a most preferred embodiment, the initialization of the pump includes a self-calibrating routine to determine internal reference parameters in the pump mechanics and administration system.

In a more preferred embodiment of the present invention, the pump comprises hydraulic actuation means, such as a flexible hose transmitting a force, for example with a hydraulic liquid, in order to pressurize and transport the medication.

Preferably, the syringe is smaller than 500 mL, such as smaller than 450 mL, such as smaller than 400 mL, such as smaller than 350 mL, such as smaller than 300 mL, such as smaller than 250 mL, such as smaller than 200 mL, such as smaller than 150, such as smaller than 100 mL, such as smaller than 50 mL. By having these volumes, it is easy to wear the pump.

In a preferred embodiment of the present invention, the pump is configured with an irreversible locking mechanism to irreversibly lock the pump to the syringe. In this, it may be difficult if not impossible to get access to the medication by tampering the device.

In a another preferred embodiment of the present invention, the medication pump and said control unit are integrated in one unit. For example, a syringe may be fixed to the control unit, or as just described above, to the pump, such that it cannot be taken apart. In another preferred embodiment of the present invention, the medication pump and said control unit are removably integrated in one unit, meaning that the pump, for example a syringe, may be removed from the control unit. In this way, it may be possible to connect another syringe to the control unit.

More preferably, the unit as just described may be a single-use system. The unit may be manufactured to only work for a single usage, whereafter it may be split apart and disposed. Most preferably, the unit is disposable, such as fully disposable, meaning that the medication pump, the administration system, for example including all electronics and for example batteries may be disposed.

In an alternative embodiment the electronics and/or batteries can be separated from the rest of the disposable system to enable separate disposal due to environmental issues.

An effect of having a disposable system and/or single use system, is that the system may be a low cost product, and at the same time, advanced enough to provide the given dosing regimen.

In some embodiments of the present invention, the administration may further comprise fastening means configured for fastening the administration system to a body or to clothes on the body. For example, the fastening means may be a clip and/or a strap.

In a preferred embodiment of the present invention, the system may be adapted for delivering the described anesthetic. Preferably, anesthetic is local and/or regional anesthetic.

In a more preferred embodiment of the present invention, the system is adapted to perform any of the methods related to the fifth aspect of the present invention.

It has previously been described that it may be possible for a person, such as a doctor, to read the dosing regimen from the control unit and/or the manual operation means.

Preferably, the control unit may be adapted to log data of said infusion of medication. For example, the control unit may be equipped with a data logger. The data logger may be used by technical personal, for example in order to test and/or to optimize the administration system. From the data logger, it may be possible to see how often a patient used the manual operation means, and/or to see if the control unit operated the pump as intended, for example with the specified dosing regimen and/or the specified power as required to operate the pump during normal circumstances.

Delivery System

Related to the fourth aspect of the present invention, the catheter is preferably a peripheral indwelling catheter or an epidural catheter. The catheter may be a catheter as described in the first aspect of the present invention. The administration system may be an administration as described above. In relation hereto, the delivery system may be adapted for delivering the described anesthetic.

Method

Related to the fifth aspect of the present invention, the method may further comprise an optional step of, not to be repeated by said administration system, infusing said medication by an infusion volume between 1-20 mL during an infusion time between 1-20 minutes with a preset infusion sequence utilizing flow rates between 30 mL/h-1200 mL/h by manually operating said pump via said control unit. In this way, it may be possible to infuse medication as desired, for example if the patient is in pain, for example pain not to be expected. Thus, if manual intervention is needed—there is an optional step of expediting the infusion by manual activation.

In a preferred embodiment of the present invention, the infusion volume and/or said infusion time and/or said period are computer implemented into said administration system.

In a more preferred embodiment of the present invention, the infusion volume and/or said infusion time and/or said period are pre-defined in said administration system.

In a yet more preferred embodiment of the present invention, the infusion volume and/or said infusion time and/or said period are user-defined in said administration system.

In a most preferred embodiment of the present invention, the infusion volume and/or said infusion time and/or said period are partly pre-defined and partly user-defined in said administration system.

In relation to the dosing, the infusion volume may be more than 1 mL, such as more than 2 mL, such as more than 3 mL, such as more than 4 mL, such as more than 5 mL, such as more than 6 mL, such as more than 7 mL, such as more than 8 mL, such as more than 9 mL, such as more than 10 mL, such as more than 11 mL, such as more than 12 mL, such as more than 13 mL, such as more than 14 mL or such as more than 15 mL, such as more than 16 mL, such as more than 17 mL or such as more than 18 mL, such as more than 19 mL or such as more than 20 mL. Alternatively and/or additionally, the infusion volume may be less than 20 mL, such as less than 19 mL, such as less than 18 mL, such as less than 17 mL, such as less than 16 mL, such as less than 15 mL such as less than 14 mL, such as less than 13 mL, such as less than 12 mL, such as less than 11 mL, such as less than 10 mL, such as less than 9 mL, such as less than 8 mL, such as less than 7 mL, such as less than 6 mL, such as less than 5 mL, such as less than 4 mL, such as less than 3 mL, such as less than 2 mL or such as less than 1 mL.

Further, the infusion time may be more than 1 min, such as more than 2 min, such as more than 3 min, such as more than 4 min, such as more than 5 min, such as more than 6 min, such as more than 7 min, such as more than 8 min, such as more than 9 min, such as more than 10 min, such as more than 11 min, such as more than 12 min, such as more than 13 min, such as more than 14 min or such as more than 15 min, such as more than 16 min, such as more than 17 min or such as more than 18 min, such as more than 19 min or such as more than 20 min. Alternatively and/or additionally, the infusion time may be less than 20 min, such as less than 19 min, such as less than 18 min, such as less than 17 min, such as less than 16 min, such as less than 15 min such as less than 14 min, such as less than 13 min, such as less than 12 min, such as less than 11 min, such as less than 10 min, such as less than 9 min, such as less than 8 min, such as less than 7 min, such as less than 6 min, such as less than 5 min, such as less than 4 min, such as less than 3 min, such as less than 2 min or such as less than 1 min.

Even further, the period may be more than 1 hour, such as more than 2 hours, such as more than 3 hours, such as more than 4 hours, such as more than 5 hours, such as more than 6 hours, such as more than 7 hours, such as more than 8 hours, such as more than 9 hours, such as more than 10 hours, such as more than 11 hours, such as more than 12 hours, such as more than 13 hours, such as more than 14 hours, such as more than 15 hours, such as more than 16 hours, such as more than 17 hours, such as more than 18 hours, such as more than 19 hours, such as more than 20 hours, such as more than 21 hours, such as more than 22 hours, such as more than 23 hours or such as more than 24 hours, such as more than 48 hours. Alternatively and/or additionally, the period may be smaller than 24 hours, such as smaller than 23 hours, such as smaller than 22 hours, such as smaller than 21 hours, such as smaller than 20 hours, such as smaller than 19 hours, such as smaller than 18 hours, such as smaller than 17 hours, such as smaller than 16 hours, such as smaller than 15 hours, such as smaller than 14 hours, such as smaller than 13 hours, such as smaller than 12 hours, such as smaller than 11 hours, such as smaller than 10 hours, such as smaller than 9 hours, such as smaller than 8 hours, such as smaller than 7 hours, such as smaller than 6 hours, such as smaller than 5 hours, such as smaller than 4 hours, such as smaller than 3 hours, such as smaller than 2 hours or such as smaller than 1 hour.

In a preferred embodiment of the present invention, the step of infusing is for pain management. However, the step of infusing may comprise a prior step of placing a catheter in fluid communication with said medication pump. The catheter may be an indwelling catheter or an epidural catheter. Preferably, the catheter may be an echogenic catheter, such that the catheter can be placed with great accuracy near a nerve to be blocked. The dosing regimen as described may be desirable and/or optimal when an echogenic catheter is placed with great accuracy in relation to the nerve to be blocked.

Preferably, the step of repeating is more than 1 time, such as more than 5 times, such as more than 10 times, such as more than 15 times, such as more than 20 times, such as more than 25 times or such as more than 50 times.

More preferably, the step of repeating is for more than 1 days, such as for more than 5 days, such as for more than 10 days, such more than 15 days, such as more than 20 days, such as more than 25 days, such as more than 30 days, such as for more than 35 days, such as for more than 40 days, such more than 45 days, such as more than 50 days, such as more than 100 days.

In a preferred embodiment of the present invention, the administration system is a wearable administration system as previously described.

Example 1—Prior Art Dosing Regimen

FIG. 1 shows how a medication is diffused around the axillary nerve in the shoulder region using a dosing regimen according to prior art. It shows two magnetic resonance images of 15 mL of local anesthetic injected over 10 seconds around a nerve in the shoulder region. The white substance represents local anaesthetic. The asterix, marked with a white arrow, represents the targeted nerve. It is clear that most of the local anesthetic is located far from the nerve, thereby not being an optimal dosing regimen.

Example 2—Dosing Regimen According to an Embodiment of the Present Invention According to several aspects of the present invention, the overall aim is to maintain a sufficiently high concentration gradient of LA close to the nerve for a prolonged time period.

Table 1 illustrates the range of volumes (1-15 mL), infusion times (0.25-10 min) and infusion rates (30-1200 mL/h) wherein the new dosing regimen according to the present invention is highlighted with bold.

TABLE 1

Range of infusion rates (mL/h) calculated from volume (mL) and infusion time (min).

| Time (min) | Volume (mL) | | | | | | |
|---|---|---|---|---|---|---|---|
| | 1 | 2 | 3 | 4 | 5 | 10 | 15 |
| 0.25 | 240 | 480 | 720 | 960 | 1200 | 2400 | 3600 |
| 0.5 | 120 | 240 | 360 | 480 | 600 | 1200 | 1800 |
| 1 | 60 | 120 | 180 | 240 | 300 | 600 | 900 |
| 2 | 30 | 60 | 90 | 120 | 150 | 300 | 450 |
| 3 | 20 | 40 | 60 | 80 | 100 | 200 | 300 |
| 4 | 15 | 30 | 45 | 60 | 75 | 150 | 225 |
| 5 | 12 | 24 | 36 | 48 | 60 | 120 | 180 |
| 10 | 6 | 12 | 18 | 24 | 30 | 60 | 90 |

Example 3—Continuous Interscalene Brachial Plexus Block

The time controlled periodic infusion regimen for this block may be: 5 ml of local anesthetic (ropivacaine 2, 5 or 7.5 mg/mL) infused over 10 min and repeated every 6 h for several days.

Example 4—Continuous Sciatic Nerve Block

The time controlled periodic infusion regimen for this block may be: 8 ml of local anesthetic (ropivacaine 2, 5 or 7.5 mg/mL) infused over 10 min and repeated every 10 h for several days.

Example 5—Epidural Analgesia for Labor

The time controlled periodic infusion regimen for this neuroaxial block may be: 10 ml of local anesthetic (bupivacaine 0.625 to 1.25 mg/mL) infused over 5-10 min and repeated every 2 h during labor.

Example 6—a Syringe

Figure 2:
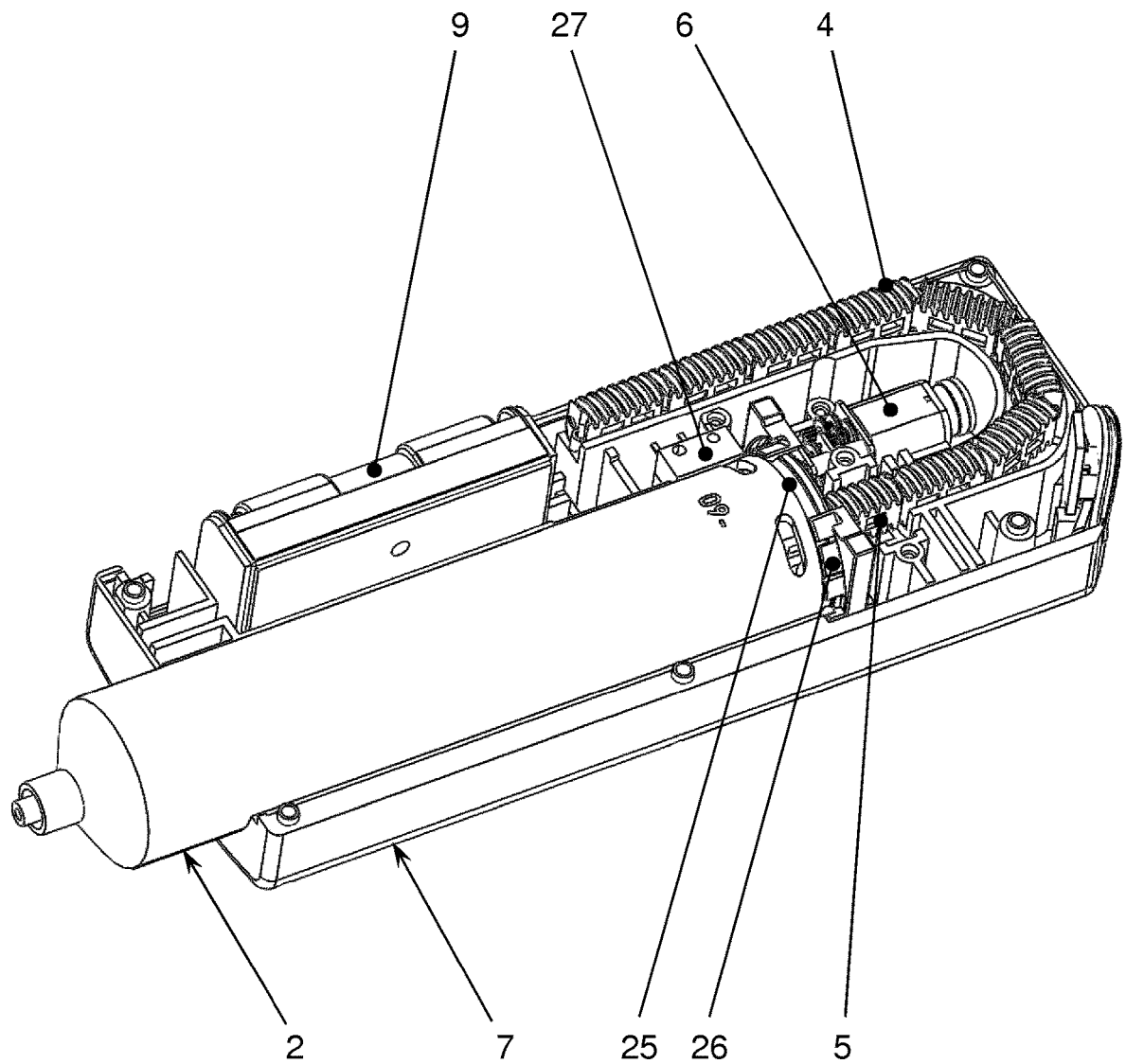
FIG. 2 shows an embodiment of the pump according to the present invention.
Figure 3:
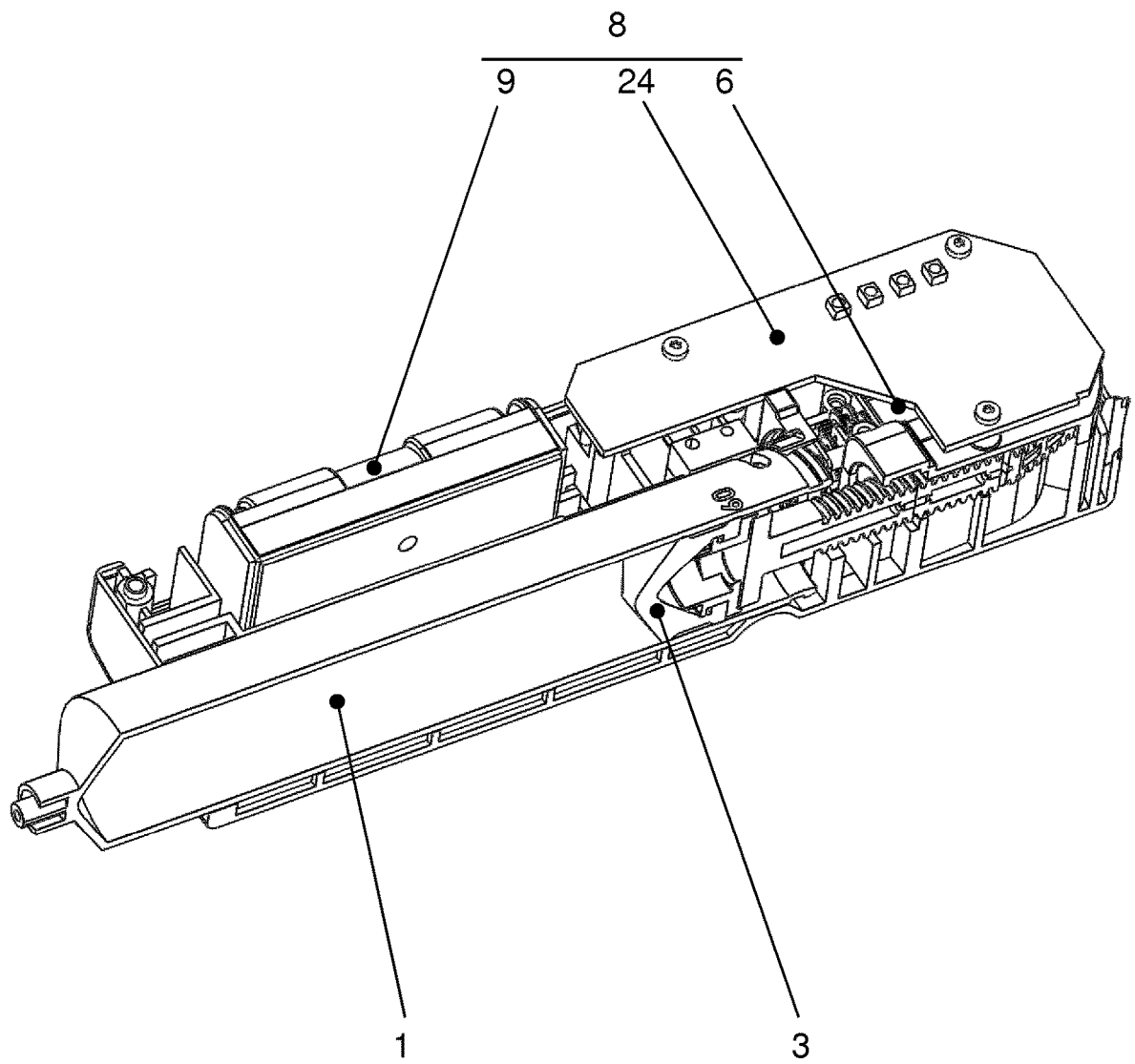
FIG. 3 shows an embodiment of the pump according to the present invention.

FIG. 2-3 shows a pump as a syringe according to the present invention. The syringe utilizes the principle of displacing the drug/liquid 1 from a syringe 2 by advancement of its piston 3. The operation of the piston can be obtained by e.g. a spindle drive, where a threaded piston rod 4 is moved by rotation of a sprocket/nut 5 connected to the piston rod with a corresponding internal thread. The sprocket/nut 5 is mechanically connected to the motorized drive means 6 which is incorporated in the same housing 7, also containing a printed circuit board (PCB) 24 and power source 9. The motorized drive 6, PCB 24 and power source 9 are main components of the pump control unit 8. The concept can be made with a rigid or flexible/hinged piston rod, which can be bent or curled in order to decrease the total length of the device while the piston 3 is retracted in the syringe barrel. The pump, or rather the control unit 8, can be programmed by the doctor or skilled operator to follow a specific dosing regimen that is selected from a list of pre-programmed options, and the patient is able to initiate a time controlled periodic infusion. In other words, the control unit 8 comprises manual setup means (not shown on this drawing), configured such that said infusion volume, and/or infusion time, and/or period is/are set up manually. The syringe 2 can be sterile and packed separately from the control unit 8, i.e. separately from the housing 7. Prior use, the pump 2 is filled directly with local anesthetics 1 by the doctor or nurse preparing the pump. The syringe 2 is then attached to the control unit 8, in this case the housing 7. To prevent refill or similar tampering of the drug content/volume, this connection could be made so it cannot be separated again once tightened preferably by means of a locking mechanism comprising a groove 25 in the syringe and a hook arrangement 26 in the pump housing or corresponding snap connections. Alternatively, the syringe 2 can be replaced by a new one. When snapped on, the syringe can activate a sensor/switch 27, triggering the control unit 8 to be powered on automatically and can be programmed to the given dosing regimen decided by the doctor. Thus, FIG. 2-3 show an example of the wearable administration system according to the present invention, configured for delivering a time-controlled periodic infusion of medication 1 to a target, comprising: a medication pump 2; a control unit 8 configured to automatically operate said medication pump to periodically infuse said medication 1 in an infusion volume between 1-20 mL during an infusion time between 1-20 minutes with a continuous flow rate between 30 mL/h-1200 mL/h and with a period of 1-48 hours. The control unit is driven by one or more batteries 9, and the control unit is configured to drive a rotating member 4, here the threaded piston rod. As described, the medication pump 2 and the control unit are here removably integrated into one unit.

Example 7—a Syringe and a Detachable Piston Rod

Figure 4:
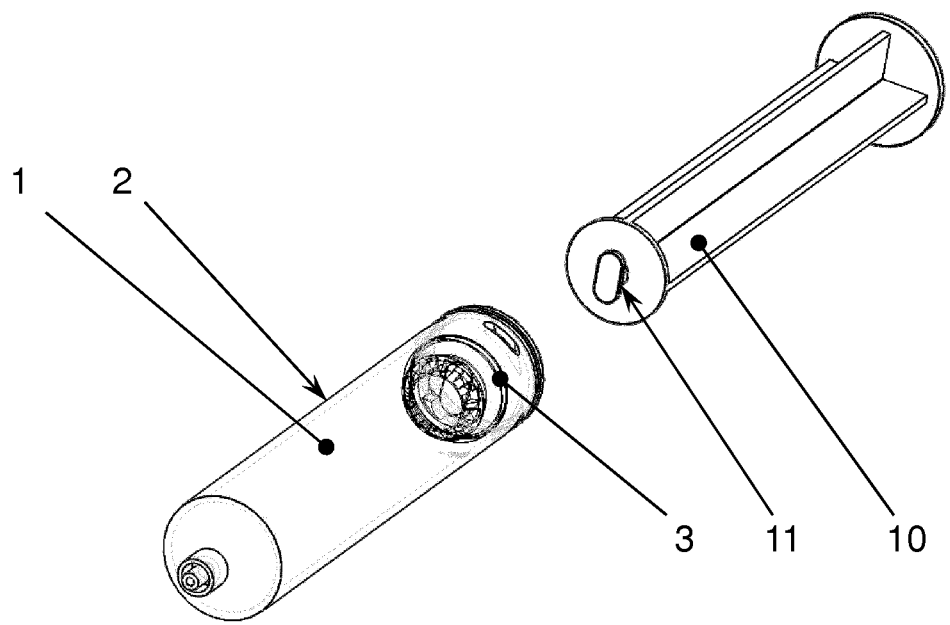
FIG. 4 shows an embodiment of the pump and the detachable piston according to the present invention from a perspective.
Figure 5:
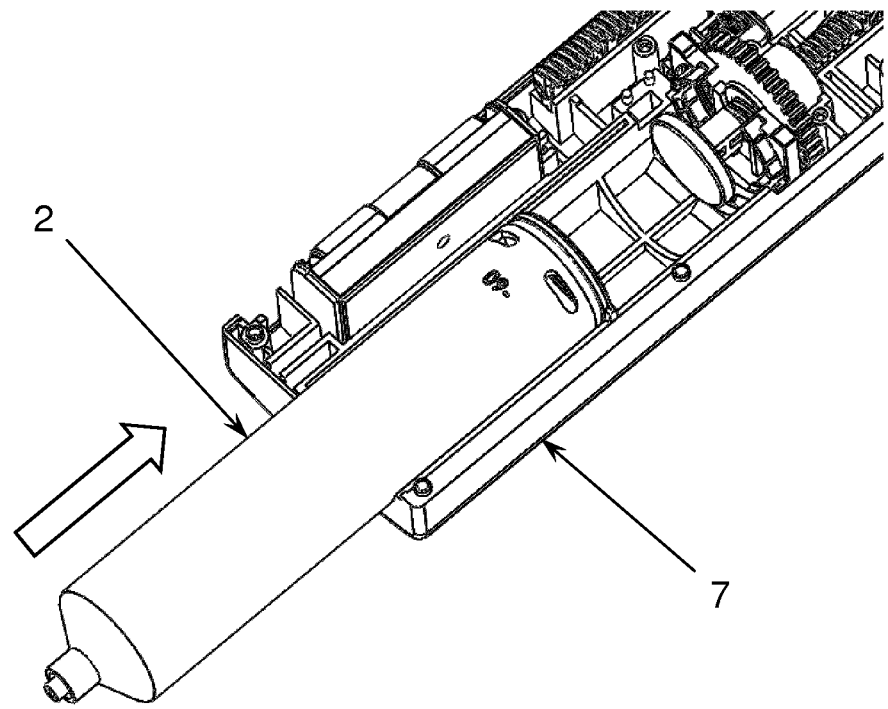
FIG. 5 shows an embodiment of the pump and the control unit according to the present invention from a perspective.

FIG. 4-5 shows the same syringe-like pump concept as mentioned in example 4, but here the syringe piston 3 is initially equipped with a temporary piston rod 10, i.e. the pump 2 comprises a detachable piston rod 10, allowing manual operation during preparation of the pump. The piston rod enables the person preparing the system to fill the syringe/reservoir 2 with drug 1 directly from the drug bulk container without any further intermediate devices such as other syringes etc. When the reservoir is filled, the temporary piston rod 10 is disconnected from the piston 3, e.g. by a bayonet coupling (turn/twist) 11 and discarded. The reservoir 2 can now be attached to the housing 7 with the control unit 8, described in example 4. Thus, FIG. 4-5 show an example of the wearable administration system according to the present invention, configured for delivering a time-controlled periodic infusion of medication 1 to a target, comprising: a medication pump 2; a control unit 8 (in the housing 7) configured to automatically operate said medication pump to periodically infuse said medication 1 in an infusion volume between 1-20 mL during an infusion time between 1-20 minutes with a continuous flow rate between 30 mL/h-1200 mL/h and with a period of 1-48 hours. The control unit is driven by one or more batteries 9 (in the housing 7) and the control unit is configured to drive a rotating member 4 (also in the housing), here the threaded piston rod. As described, the medication pump 2 and the control unit 8 (in the housing 7) are here removably integrated into one unit.

Example 8—a Peristaltic Pump

Figures 6, 7:
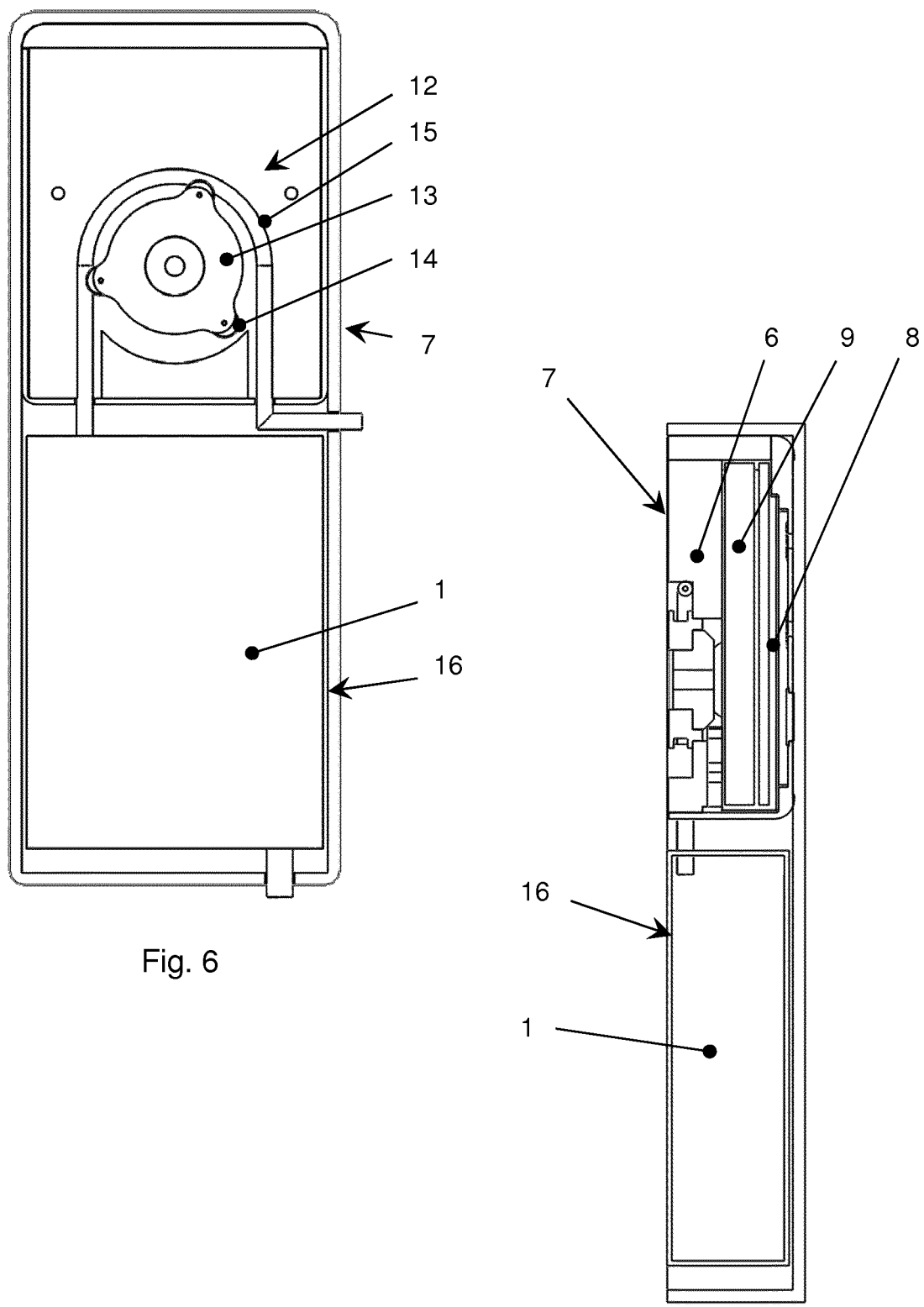
FIG. 6 shows an embodiment of the pump according to the present invention from the front.
FIG. 7 shows the same embodiment as in FIG. 5 of the pump according to the present invention from a side.

FIG. 6 and FIG. 7 show a peristaltic pump 12 in a housing 7 comprising mechanical drive means 6, control unit 8 and power source 9. The rotation wheel 13 with rollers 14 compresses a soft tube 15 and thus creating a displacement of the liquid in the internal lumen of the tube. The pump will be in fluid connection to a reservoir 16 containing the drug 1 e.g. anesthetics or other medication. This container can be incorporated into the final pump design, either permanently or as a "click-on" unit, handled and filled separated from the pump unit. Thus, FIG. 6 and FIG. 7 show an example of the wearable administration system according to the present invention, configured for delivering a time-controlled periodic infusion of medication to a target, comprising: a medication pump 2 (here the a peristaltic pump 12); a control unit 8 (in the housing 7) configured to automatically operate said medication pump to periodically infuse said medication 1 in an infusion volume between 1-20 mL during an infusion time between 1-20 minutes with a continuous flow rate between 30 mL/h-1200 mL/h and with a period of 1-48 hours. The control unit 8 is driven by one or more batteries 9 (in the housing 7), and the control unit 8 is configured to drive a rotating member 13 (here a rotation wheel).

Example 9—Use of Pump

Figure 8:
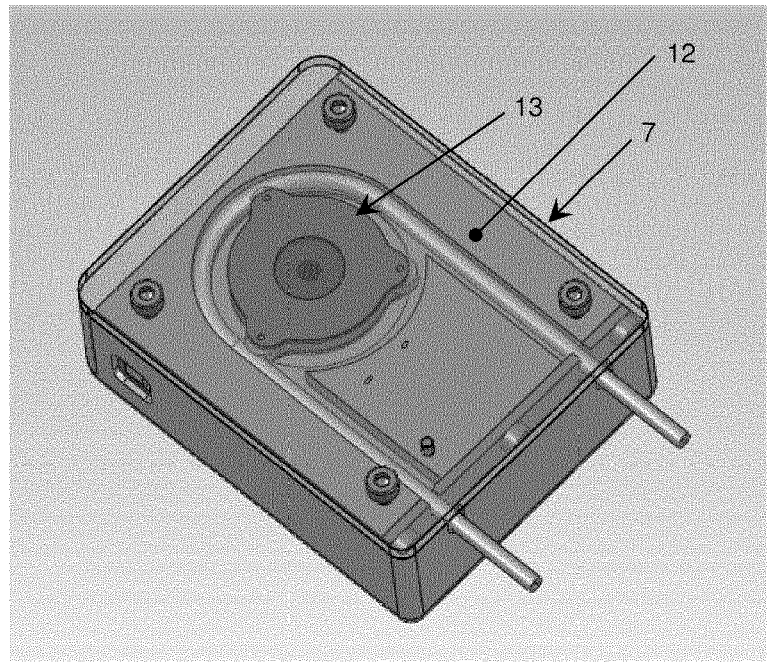
FIG. 8 shows an embodiment of the pump according to the present invention from a first perspective.
Figure 9:
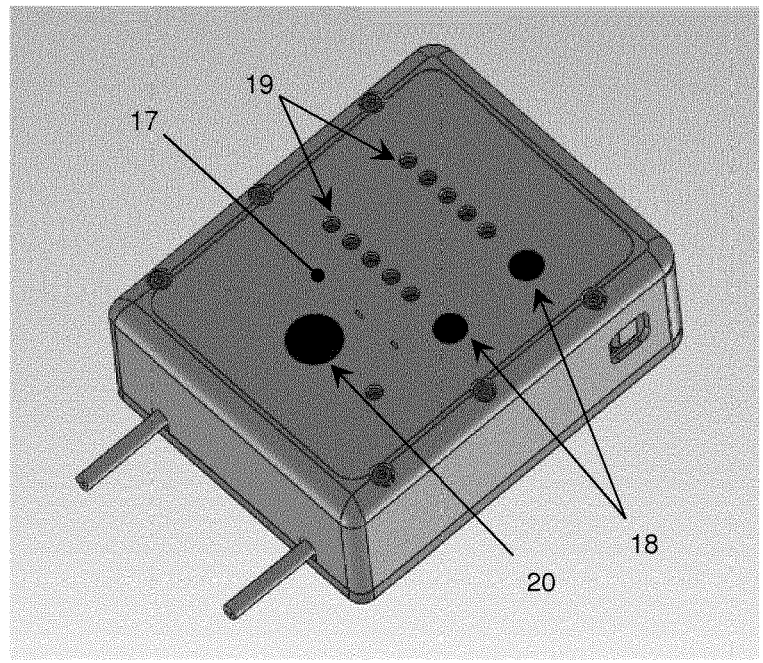
FIG. 9 shows the same embodiment as in FIG. 6 of the pump according to the present invention from a second perspective.
Figure 10:
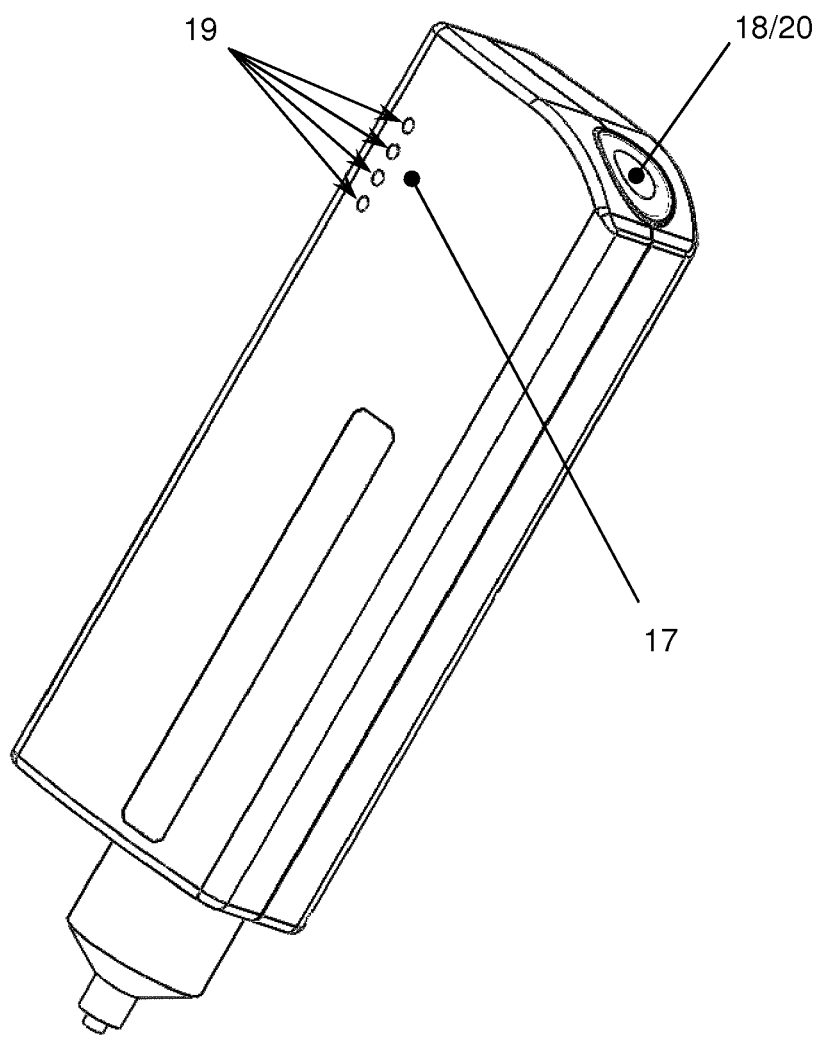
FIG. 10 shows an embodiment of the pump according to the present invention from a perspective.

FIG. 8, FIG. 9 and FIG. 10 show one possible design of the pump housing 7, where a user interface 17 is incorporated at one side of the housing, e.g. opposite a peristaltic pump 12 or syringe pump 2. A limited set of adjustments to the pre-programmed dosing regimen can be performed on the pump by the doctor or skilled operator prior to activation, depending on anatomical site and patient characteristics. The adjustable parameters could be e.g. time between each dose and volume of individual dose given and is selected by pushing one or more button(s) 18. The selected setting is indicated by one or multiple illuminated LED's 19. In addition, the patient will be able to press a button 20 that, when pressed for prolonged time, e.g. 2 seconds, will initiate a fast infusion of a preset volume of local anesthetics. Thus, FIG. 8, FIG. 9 and FIG. 10 show an example of the wearable administration system according to the present invention, configured for delivering a time-controlled periodic infusion of medication to a target, comprising: a medication pump 2 (here the peristaltic pump 12 and a syringe pump 2); a control unit 8 (in the housing 7) configured to automatically operate said medication pump to periodically infuse said medication 1 in an infusion volume between 1-20 mL during an infusion time between 1-20 minutes with a continuous flow rate between 30 mL/h-1200 mL/h and with a period of 1-48 hours. The control unit comprises manual setup means 18, configured such that said infusion volume, and/or infusion time and/or period is/are set up manually. Further, the control unit comprises manual operation means 20, configured such that when manually operated, said control unit is configured to operate said medication pump to infuse said medication in an infusion volume between 1-20 mL during an infusion time between 1-20 minutes with a continuous flow rate between 30 mL/h-1200 mL/h. The control unit 8 is driven by one or more batteries 9 (in the housing 7), and the control unit 8 is configured to drive a rotating member 13 (here a rotation wheel).

Example 10—Hydraulic Activated Pump

Figure 11:
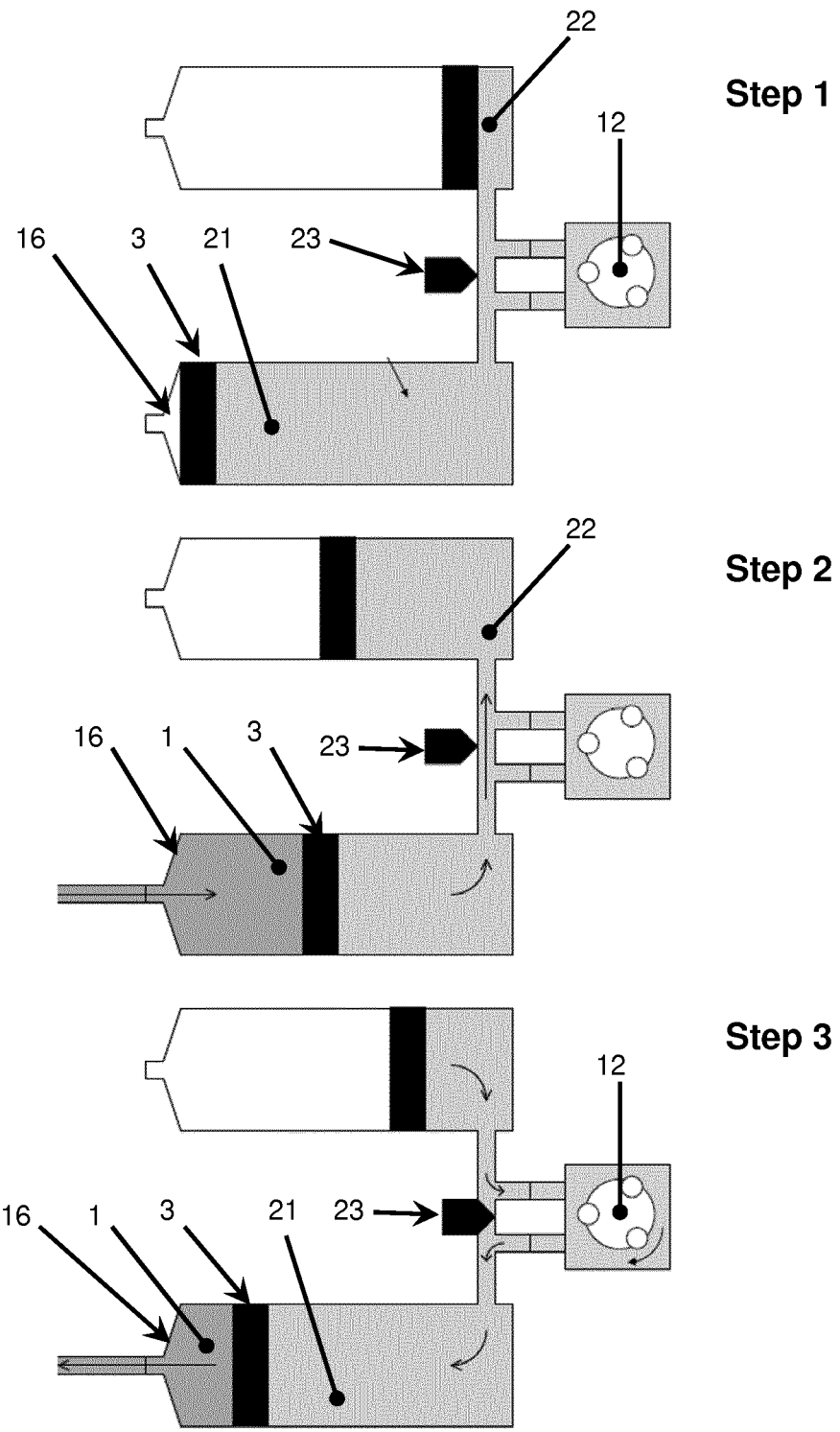
FIG. 11 shows an embodiment of the method according to the present invention.

FIG. 11 shows a hydraulic activated pump concept in three different stages of operation. This example described an embodiment of the hydraulic actuation means. A hydraulic activated pump eliminates the need for a piston rod to activate the piston which controls the flow of drug. The media transmitting the force is now a flexible hose and not a rigid mechanical connection. This is beneficial in regards to a compact design.

Step 1: The drug reservoir 16 is empty and the piston 3 is fully advanced. The space behind the piston is pre-filled with a hydraulic suitable liquid 21, e.g. sterile saline. The space mentioned is in fluid connection with a buffer reservoir 22 via a peristaltic pump 12 and a by-pass valve 23, shown open.

Step 2: Filling the drug reservoir 16 with drug 1. Hereby the piston 3 moves backwards, displacing the liquid through the open by-pass valve into the buffer reservoir 22.

Step 3: During dosage use, the by-pass valve 23 is closed and the hydraulic liquid 21 is pumped back by the peristaltic pump 12 into the space behind the drug reservoir end thus displacing the piston 3 forward in the syringe 2, forcing the drug 1 out of the drug reservoir 16.

The buffer reservoir can be like a syringe or a pouch or other containers with a flexible volume.

Thus, FIG. 11 shows an example of the wearable administration system according to the present invention, configured for delivering a time-controlled periodic infusion of medication to a target, comprising: a medication pump 2 (here the a peristaltic pump 12); a control unit (not shown in the drawing) configured to automatically operate said medication pump to periodically infuse said medication 1 in an infusion volume between 1-20 mL during an infusion time between 1-20 minutes with a continuous flow rate between 30 mL/h-1200 mL/h and with a period of 1-48 hours.

Example 11—Principle of Administering Drug

Figure 12:
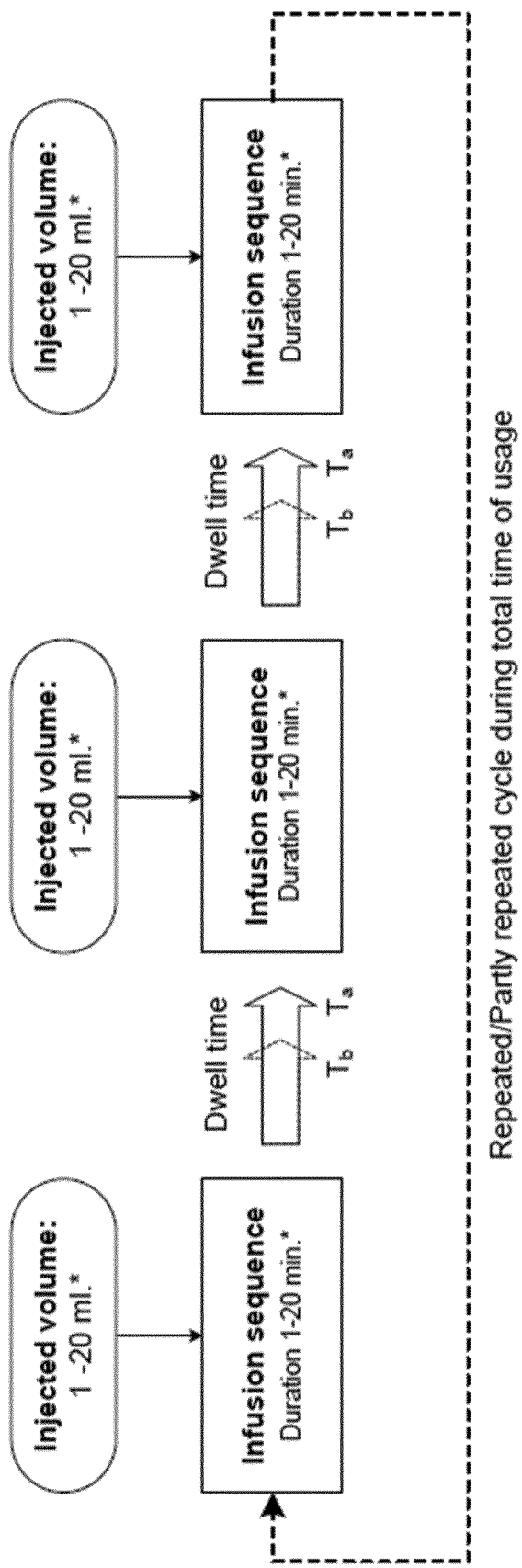
FIG. 12 shows an example how the infusion sequence can be repeated according to the present invention.
Figure 13:
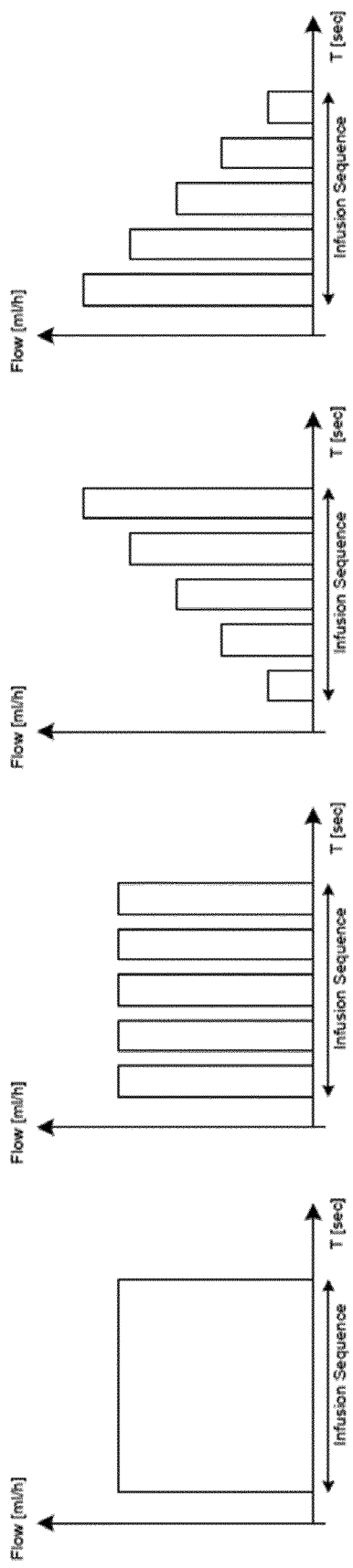
FIG. 13 shows several embodiments of the infusion sequence according to the present invention.
Figure 13:
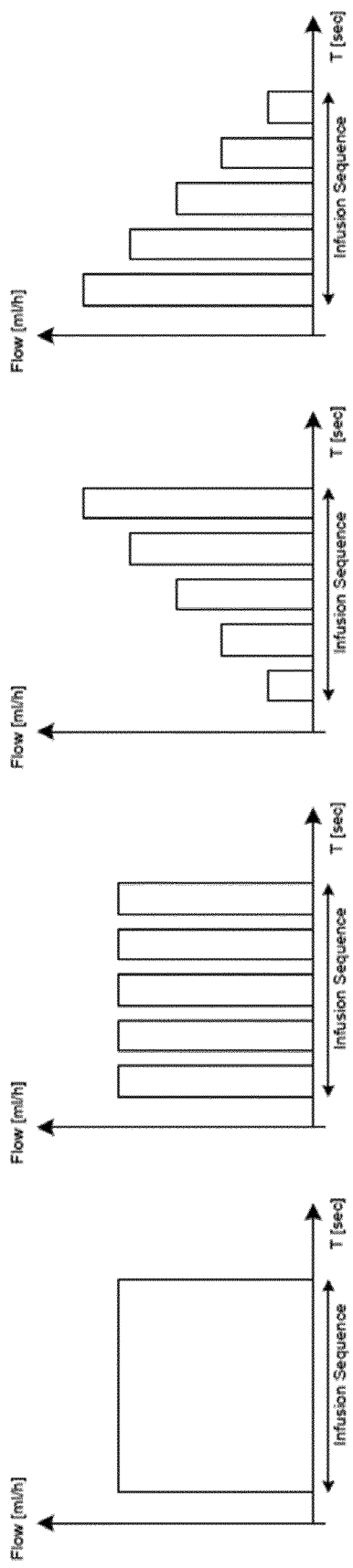
Figure 13:
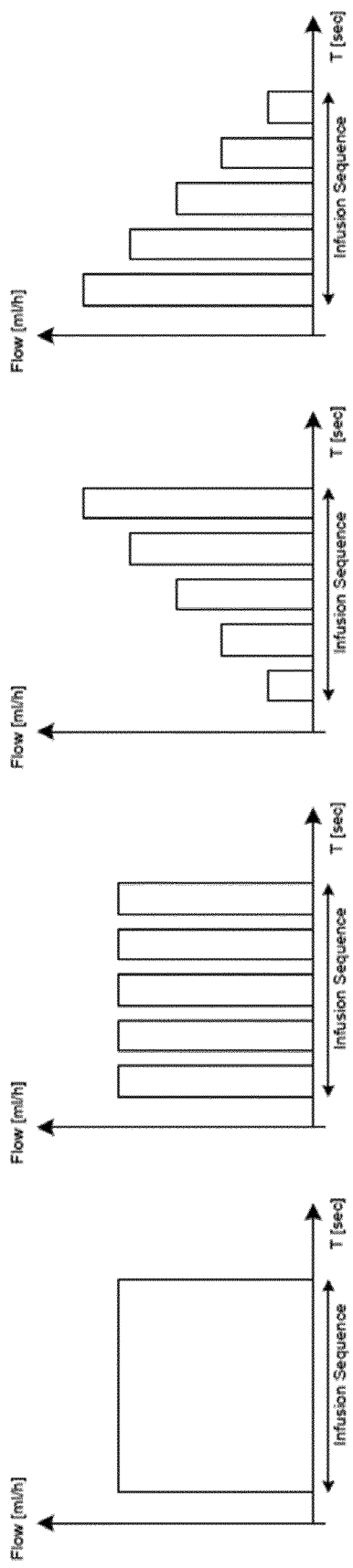
Figure 13:
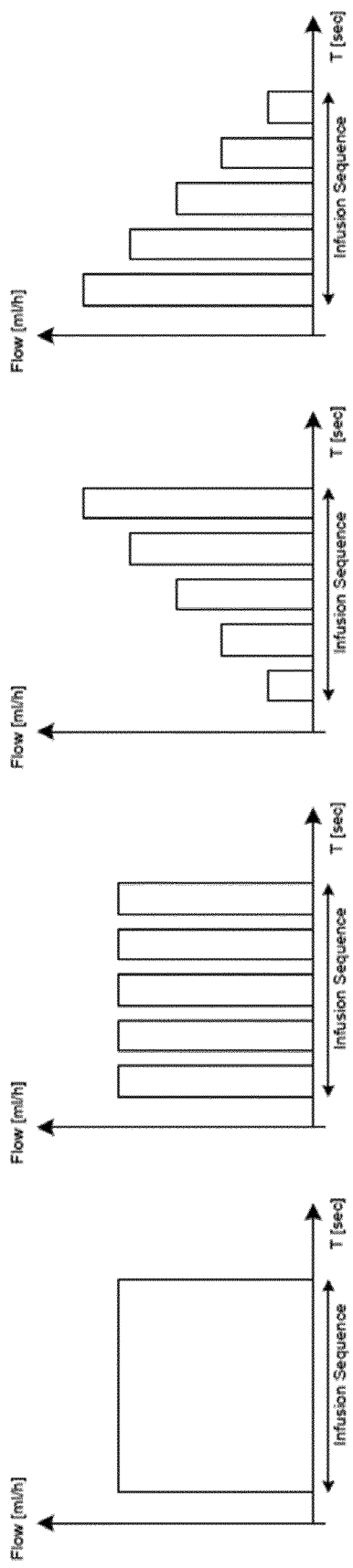
Figure 13:
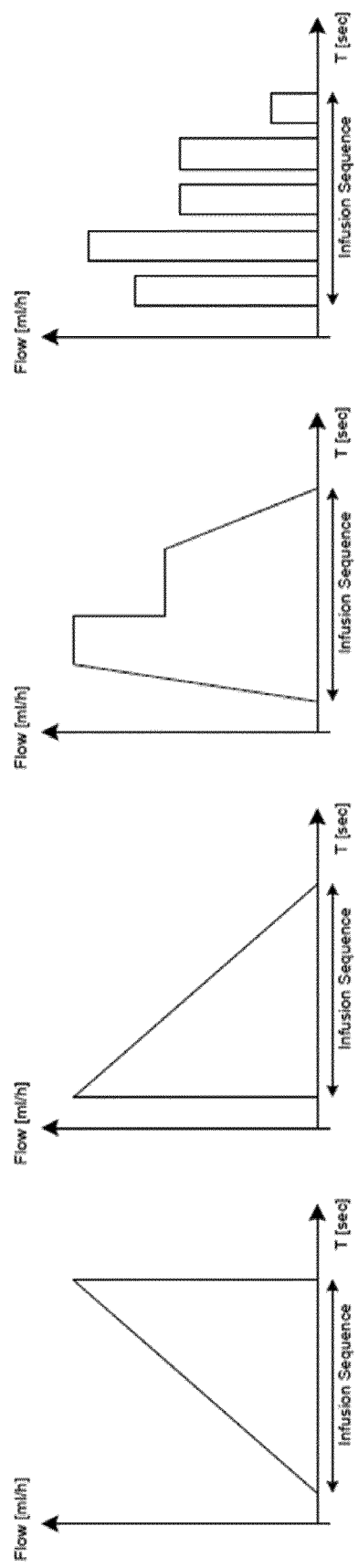
Figure 13:
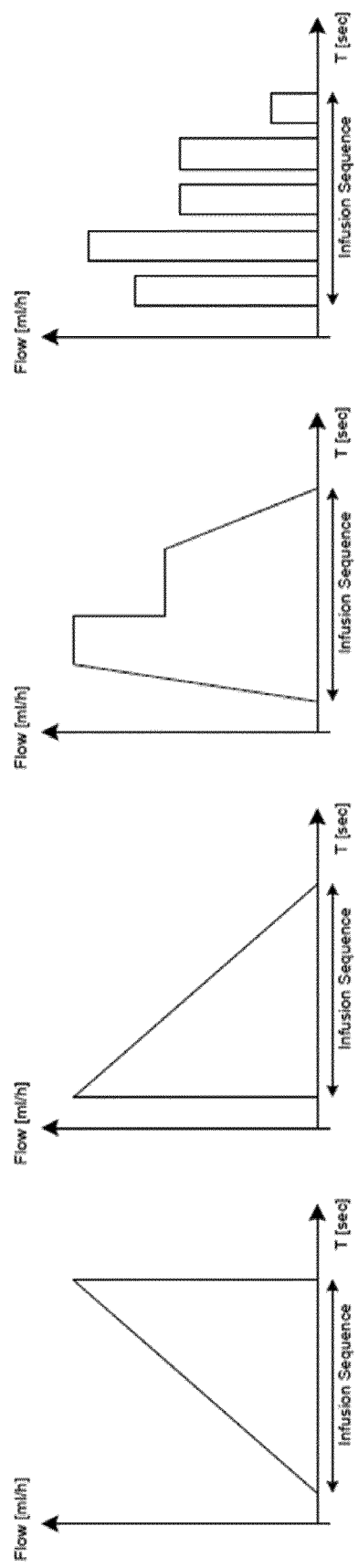
Figure 13:
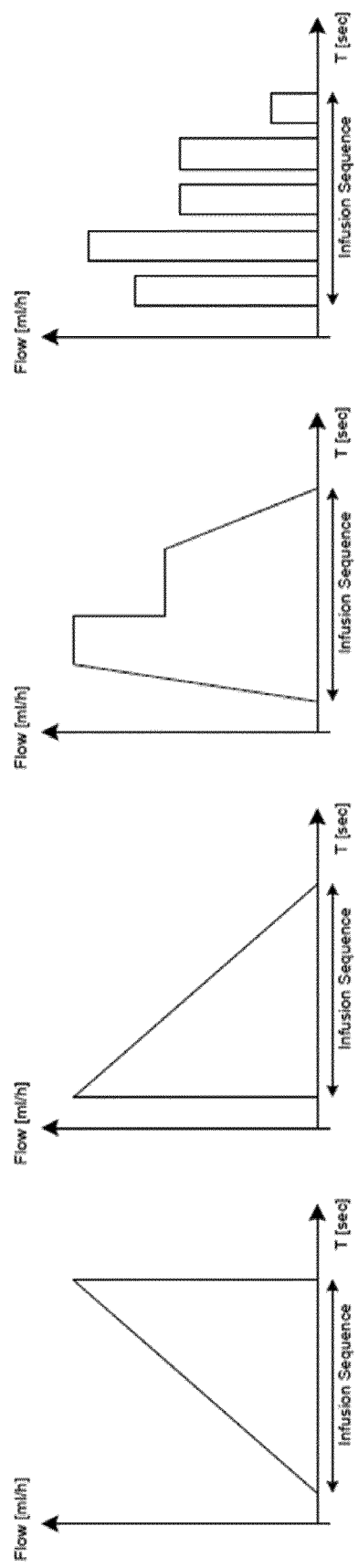
Figure 13:
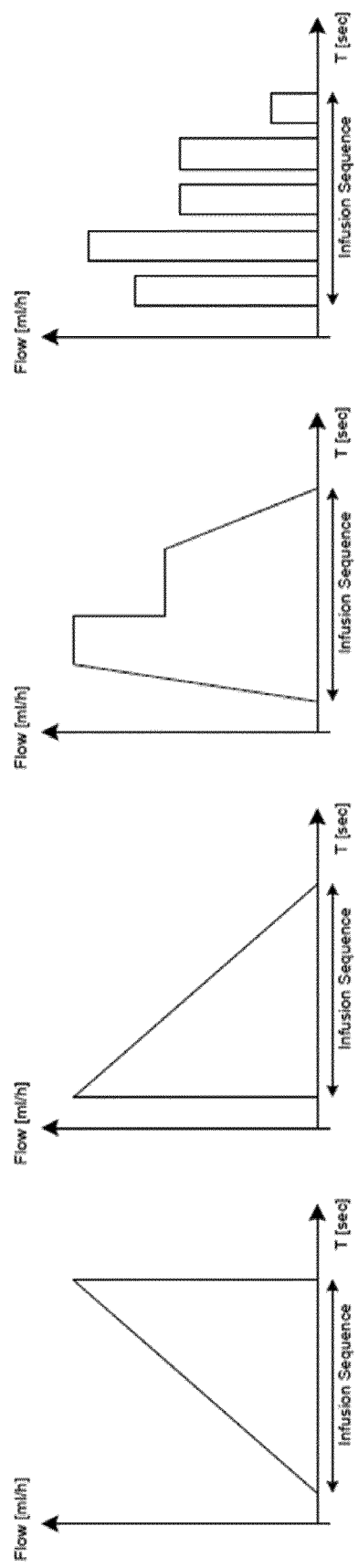

FIG. 12 shows a schematic chart of the cycle of dosing regimen. The pre-set volume of drug is infused over a pre-set time span during an infusion sequence. Different infusion sequences are shown in FIG. 13. The infusion sequence may depend on anatomy and rigidity of tissue surrounding the nerve.

FIG. 13a shows an infusion sequence with a constant flow rate.

FIG. 13b shows an infusion sequence with a pulse train including a number of short pulses with identical flowrates separated by short pauses defined within the infusion sequence.

FIG. 13c shows an infusion sequence with a pulse train including a number of short pulses with increasing flowrates separated by short pauses defined within the infusion sequence.

FIG. 13d shows an infusion sequence with a pulse train including a number of short pulses with decreasing flowrates separated by short pauses defined within the infusion sequence.

FIG. 13e shows an infusion sequence with an uninterrupted infusion with increasing flowrate within the infusion sequence.

FIG. 13f shows an infusion sequence with an uninterrupted infusion with decreasing flowrate within the infusion sequence.

FIG. 13g shows an infusion sequence combining pattern 12a, 12e and 12f within the infusion sequence.

FIG. 13g shows an infusion sequence combining pattern 12b, 12c and 12d within the infusion sequence.

After completion of an infusion sequence, the system may wait a preset period of time, FIG. 12 "$T_a$", before a next infusion sequence is performed. These steps may then be repeated during the time of pump operation. The parameters, such as the preset period of time, may be static (same during the complete operating time of the device) or dynamic, or may be altered by the controlling software according to the preset infusion sequence. Alternatively, the parameters may be "intelligent" based on a software algorithm, such as evaluating a potential (repeated) difference between the preset dwell-time $T_a$ and the time span before a manual activation of the pump. The manual activation of the pump may for example be activated by an actual user in pain. Accordingly, the dwell time may be altered by a new time, thereby overriding the preset dwell-time, shown in FIG. 12 as "$T_b$". This difference may trigger an automatic adjustment of the preset value for the duration of the dwell time.

Thus, FIG. 12 and FIG. 13 show an overview of the method according to the present invention, specifically, a method for delivering a time-controlled periodic infusion of medication from a wearable administration system comprising a medication pump and a control unit, comprising the steps of: infusing said medication by an infusion volume between 1-20 mL during an infusion time between 1-20 minutes with a continuous flow rate between 30 mL/h-1200 mL/h by automatically operating said pump via said control unit; waiting a period of 1-48 hours; and repeating the steps. The pumps as described in the examples 2-10 may all work by the principle as shown in this example.

The invention claimed is:

1. A wearable administration system configured for delivering a time-controlled periodic infusion of medication to a target, comprising:
  a medication pump;
  a control unit configured to automatically operate said medication pump to periodically infuse said medication utilizing flow rates between 30 mL/h and 1200 mL/h to define a preset infusion sequence with an infusion volume of between 1-20 mL during an infusion time of between 1-20 minutes with a period of 1-48 hours.

2. The administration system according to claim 1, wherein said control unit comprises manual operation means, configured such that when manually operated, said control unit is configured to operate said medication pump to infuse said medication utilizing flow rates between 30 mL/h and 1200 mL/h to define a preset infusion sequence with an infusion volume of between 1-20 mL during an infusion time of between 1-20 minutes with a period of 1-48 hours.

3. The administration system according to claim 1, wherein the control unit is further configured to automatically operate said medication pump to periodically infuse a plurality of infusion sequences such that each of said infusion sequences are separated by a preset dwell-time that is different from the period.

4. The administration system according to claim 3, wherein the control unit is configured to alter the preset dwell-time if being operated manually.

5. The administration system according to claim 1, wherein said control unit comprises manual setup means, configured such that said infusion volume, and/or infusion time and/or period is/are set up manually.

6. The administration system according to claim 5, wherein said manual setup means is configured to be set up such that said infusion volume, and/or infusion time and/or period is/are locked.

7. The administration system according to claim 1, wherein said control unit is driven by one or more batteries and/or a portable power source.

8. The administration system according to claim 1, wherein said medication pump and said control unit are integrated in one component.

9. The administration system according to claim 8, wherein said component is disposable.

10. The administration system according to claim 8, wherein said component is a single-use system.

11. The administration system according to claim 1 further comprising fastening means configured for fastening the administration system to a body or to clothes on the body.

12. The administration system according claim 1, wherein said medication pump and said control unit are removably integrated in one unit.

13. A delivery system for delivering a time-controlled periodic infusion of medication to a target, comprising:
  a wearable administration system according to claim 12; and
  a catheter.

14. The delivery system according to claim 13, wherein said catheter is a peripheral indwelling catheter or an epidural catheter.

15. A method for delivering a time-controlled periodic infusion of medication to a target from a wearable administration system comprising a medication pump and a control unit, comprising:
  a) infusing said medication utilizing flow rates between 30 mL/h and 1200 mL/h to define a preset infusion sequence with an infusion volume of between 1-20 mL during an infusion time of between 1-20 minutes by automatically operating said pump via said control unit;
  b) waiting a period of 1-48 hours; and
  c) repeating a-b.

16. The method according to claim 15, further comprising optionally, not to be repeated by said administration system, infusing said medication utilizing flow rates between 30 mL/h and 1200 mL/h to define a preset infusion sequence with an infusion volume of between 1-20 mL during an infusion time of between 1-20 minutes by manually operating said pump via said control unit.

17. The method according to claim 15, wherein said infusion volume and/or said infusion time and/or said period are computer implemented into said administration system.

18. The method according to claim 15, wherein said infusion volume and/or said infusion time and/or said period are pre-defined in said administration system.

19. The method according to claim 15, wherein said infusion volume and/or said infusion time and/or said period are user-defined in said administration system.

* * * * *